(12) United States Patent
Seguin et al.

(10) Patent No.: US 6,197,986 B1
(45) Date of Patent: Mar. 6, 2001

(54) COMPOUNDS CONTAINING BIOLOGICALLY ACTIVE SILICON, WHICH ARE UNDER SOLID FORM

(75) Inventors: Marie-Christine Seguin; Jean Gueyne, both of Monaco (FR)

(73) Assignee: Exsymol S.A.M., Monaco (FR)

( * ) Notice: Subject to any disclaimer, the term of this patent is extended or adjusted under 35 U.S.C. 154(b) by 0 days.

(21) Appl. No.: 09/046,514

(22) Filed: Mar. 24, 1998

(30) Foreign Application Priority Data

Mar. 24, 1997 (FR) .................................................. 97 03792

(51) Int. Cl.$^7$ ...................................................... C07F 9/02
(52) U.S. Cl. .......................... 556/405; 556/401; 556/404; 424/400; 424/401
(58) Field of Search .................................. 424/400, 401; 556/400, 401, 482, 465

(56) References Cited

U.S. PATENT DOCUMENTS

| | | | |
|---|---|---|---|
| 4,324,250 | 4/1982 | Braun et al. | 128/395 |
| 4,985,405 | 1/1991 | Gueyne et al. | 514/8 |
| 5,037,803 | 8/1991 | Gueyne et al. | 514/2 |

FOREIGN PATENT DOCUMENTS

| | | |
|---|---|---|
| 0 289 366 A1 | 11/1988 | (EP) . |
| 2 158 068 | 6/1973 | (FR) . |
| 2 254 803 | 11/1980 | (FR) . |
| 2 561 915 | 10/1985 | (FR) . |
| 2 610 522 | 8/1988 | (FR) . |
| 1 388 330 | 3/1979 | (GB) . |
| 2 159 409 | 12/1985 | (GB) . |
| 61129185 | * 6/1986 | (JP) . |
| 63008390 | * 6/1986 | (JP) . |

OTHER PUBLICATIONS

André Franco, "I Silanoli Procosmetici," *Cosmet. News*, 88 vol. 60:163–8 (May–Jun. 1998).
Patent Abstracts of Japan, vol. 12, No. 209 "Composition containing silicon compound," JP 63–008,390 (Jan. 14, 1988).
Chemical Abstracts, vol. 106:67477m, Noda et al. "Organosilanol Compositions," JP 61–129,185 (Jun. 17, 1986).
Chemical Abstracts, vol. 106:67478n, Noda et al. "Organosilanol Compositions," JP 61–129,186 (Jun. 17, 1986).

* cited by examiner

*Primary Examiner*—Dameron Jones
(74) *Attorney, Agent, or Firm*—James C. Lydon

(57) ABSTRACT

Organo silicon compound having the following general formula (I):

$$R_4\text{—Si}(OR_1)(OR_2)(R_3) \qquad (I)$$

where
  $R_1$ and $R_2$ each one independently represent an atom of hydrogen or an alkyl group,
  $R_3$ represents an hydrogen atom, an hydroxyl group, an amine group, an alkyl group, an alkoxy or a carboxylate group,
  and at least one of the $OR_1$, $OR_2$ or $R_3$ groups represents an hydroxyl group,
  $R_4$ represents an alkyl group substituted or not by a functional group such as, notably, an alkyl phosphate group or an alkyl phosphonate group, or any other group for which the $R_4$—Si bond is not hydrolyzable,
and the compound:
  is in solid form,
  and/or is possibly associated with at least one stabilizer,
  and/or is possibly associated with at least one dispersant.

11 Claims, No Drawings

COMPOUNDS CONTAINING BIOLOGICALLY ACTIVE SILICON, WHICH ARE UNDER SOLID FORM

The present invention concerns compounds containing biologically active silicon, which are under solid form, as well as pharmaceutical and cosmetic composition containing these compounds.

BACKGROUND OF THE INVENTION

The compounds containing biologically active silicon are organo silicon compounds and more especially silanols bearing several Si—OH bonds. Silanols are described in the prior art as constituting a form of silicon assimilable by the organism, given that they have the property of existing as oligomer soluble form in aqueous solution with a low molecular weight (EP-0 289 366).

Until now, biologically active silicon compounds have been available only as diluted solutions, since they polymerize when too much concentrated, and until now, all attempts to obtain these compounds by eliminating water have invariably led to their polymerization and thus to the loss of their biological properties. The fact that these organo silicon compounds of the prior art exist only as diluted solutions limits their use and particularly make impossible their incorporation in cosmetic or pharmaceutical compositions under non aqueous form or tablets or pills to be administered orally.

Thus, to notably remedy these drawbacks, one of the main goal of the invention is to obtain a biologically active organo silicon compound under a solid form.

SUMMARY OF THE INVENTION

The organo silicon compound according to the invention has the following general formula (I):

$$R_4\text{—Si (OR}_1\text{) (OR}_2\text{) (R}_3\text{)} \qquad (I)$$

wherein $R_1$ and $R_2$ each one independently represent an atom of hydrogen or an alkyl group, $R_3$ represents an hydrogen atom, an hydroxyl group, an amine group, an alkyl group, an alcoxy or a carboxylate group, and at least one of the $OR_1$, $OR_2$ or $R_3$ groups represents an hydroxyl group, $R_4$ represents an alkyl group substituted or not by a functional group such as, notably, an alkyl phosphate group or an alkyl phosphonate group, or any other group for which the $R_4$—Si bond is not hydrolyzable, and the said compound:

is under solid form,
and/or is possibly associated with at least one stabilizer,
and/or is possibly associated with at least one dispersant.

Preferably, the compound according to the invention is a compound of formula (I) wherein $R_4$ represents a diethylphosphatoethyl group and/or $OR_1$, $OR_2$ and $R_3$ groups represent each an hydroxyl group.

According to an embodiment of the invention, the stabilizer is a carboxylic acid, an amino acid or a derived amino acid, a peptide or a protein, an alcohol or a polyol, a polysaccharide, and/or their salts.

Preferably, the carboxylic acid and/or its salt is aspartic acid, glutamic acid, lactic acid, salicylic acid, theophylline acetic acid, carboxylic pyrrolidinone acid and/or their salts.

Preferably, the amino acid and/or its salt is arginine, serine, threonine, hydroxyproline, acetylmethionine, acetyl tyrosine and/or their salts.

Preferably, the peptide is a polypeptide derived from elastin proteins, spirulina, collagen, or vegetal proteins, e.g. oat or wheat proteins.

Advantageously, this polypeptide is hydrolized elastin proteins, hydrolysed spirulina, hydrolysed collagen, or hydrolysed vegetal proteins, e.g. oat or wheat proteins.

Preferably, the protein is an elastin protein, spirulina protein, collagen protein, or a vegetal protein, e.g. oat or wheat protein.

Advantageously, the polyol is lactose.

Preferably, the polysaccharide is a glycosaminoglycanne, a mucopolysaccharide such as particularly hyaluronic acid, pectin or alginic acid.

According to another embodiment of the invention, the dispersant is a polyamiole, a carbohydrate, a polysaccharide, a polyoxethylene such as polyethylene glycol or a non water soluble (or weakly water soluble) fatty compound e.g. a triglyceride.

Another goal of the invention is to propose a pharmaceutical or a cosmetic composition including such a compound, in association with any suitable excipient, and being administered orally, in order to be used in ambulatory medication which does not require the realization of previous medical treatment.

The invention will be better understood after the lecture of the following detailed description; its purpose is to illustrate and to explain, without limitation, the invention.

DETAILED DESCRIPTION OF THE PREFERRED EMBODIMENTS

The compound according to the invention conforms to the general formula (I) wherein $R_1$ and $R_2$ each one independently represent an hydrogen atom or an alkyl group, preferably a $C_{1-4}$ alkyl group, $R_3$ represents an hydrogen atom, an hydroxyl group, an amine group, an alkyl group, preferably a $C_{1-4}$ alkyl group, an alkoxy group, preferably a $C_{1-4}$ alkoxy or carboxylate group preferably bonded to the silicon through an oxygen atom, and at least one of the $OR_1$, $OR_2$ or $R_3$ group represents an hydroxyl group, $R_4$ represents a substituted or unsubstituted alkyl group e.g. an alkylophosphate group, preferably a $C_{1-4}$ alkyl phosphate or an alkyl phosphonate group preferably a $C_{1-4}$ alkyl phosphonate, or any other group for which the $R_4$—Si bond is not hydrolyzable, this compound having a main characteristic, which is to be in a solid form. This compound can also, but not necessarily be associated with at least a stabilizer. It can also, but not necessarily, be associated besides, or alternatively with at least one dispersant.

The preferred compounds of the invention are the ones of formula (I) wherein $R_4$ represents a diethylphosphatoethyl group. Among these compounds, the diethylphosphatoethylsilanetriol can be distinguished as the most preferred compound.

One characteristic of the compound according to the invention is that a part of the substituents of the silicon atom can, in contact with a molecule of water, hydrolyse spontaneously in order to form a supplementary Si—OH bond, which will contribute to reinforce the in vivo activity of the said compounds.

The stabilizer is a polar compound which can form weak bonds (hydrogen bonds) or strong bonds (covalent bonds) with the organo silicon compound. The stabilizer opposes the formation of a siloxane Si—O—Si bond leading to insoluble or slightly water soluble polysiloxanes compounds. It will contribute to avoid the polymerization of the organo silicon compound.

For example, the stabilizer can be a carboxylic acid or its salt, e.g. aspartic acid, glutamic acid, lactic acid, salicylic acid, theophylline acetic acid, pyrrolidone carboxylic acid and/or their salts.

The stabilizer can also be an amino acid or a derived amino acid and/or their salts. Among these amino acids, serine, threonine, hydroxyproline, acetylmetionine, acetyl tyrosine and/or their salts are preferred.

Hydroxyproline is especially interesting, notably because of its regenerating activity of the connective tissue. It is naturally present in great quantity in collagen.

As well, acetyl tyrosine is notably interesting for its role in melanogenesis.

Thus, the stabilizer can also be a peptide or a protein. Among peptides, polypeptides derived from elastin, spirulina, collagen as well as polypeptides derived from vegetal proteins e.g. oat and wheat proteins are preferred. Advantageously, among these polypeptides those which result from the lysis or hydrolysis of proteins have been chosen. Notably, good results in matter of stabilization are obtained with hydrolyzed wheat protein.

As well, the stabilizer can be a protein, and in this case, elastin, spirulina and collagen proteins as well as vegetal proteins e.g. oat and wheat proteins, are preferred.

The stabilizer can also be an alcohol or a polyol such as lactose. The stabilizer can also be a polysaccharide. Among polysaccharides, glucosaminoglycanes, mucopolysaccharides e.g. hyaluronic acid, pectin and alginic acid are preferred.

A good stabilizer, for example, is the above mentioned hyaluronic acid, which is in fact the acidic mucopolysaccharide resulting from the reaction between N-acetyl-glucosamine and the glucuronic acid.

All these compounds are chosen as stabilizers because they have the above mentioned properties, and also because they are commonly used in cosmetics.

According to a special embodiment of the invention, the organo silicon compound can also be associated with a dispersant. The purpose of the dispersant is to dilute the organo silicon compound and to oppose its polycondensation. Thus, the dispersant is under the form of a more or less inert matrix intended to dilute, in the powder, the organo silicon compound molecules. Eventhough its chemical formula is sometimes very similar to that of the stabilizer, the dispersant does not contribute to the direct stabilisation of the organo silicon compound: it acts mainly through a dilution effect.

The addition of a dispersant can also be motivated by considerations linked to the formulation of compositions according to the invention.

According to an other embodiment of the invention, the dispersant is a polyamide, a carbohydrate, a polysaccharide, a polyoxyethylene such as a polyethylene glycol or a fatty compound not soluble or slightly soluble in water such as particularly a triglyceride. Advantageously, the carbohydrate is sorbitol. Preferably, the polysaccharide is cellulose.

The dispersant and the stabilizer can have common physico-chemical properties.

In presence of water and/or in vivo, the compound leads to the formation of silanols under a soluble aqueous form presenting the properties of the silanols of the prior art. However, whatever the silicon derivatives used for the preparation of the compound according to the invention, it has been noticed that the silanol released after hydrolysis is not necessarily the complete and direct product of hydrolysis of the said starting derivative.

According to an advantageous embodiment of the invention, the content in silicon in the compounds according to the invention varies between 0.1 and 10% in weight, preferably between 1 and 5% in weight.

The following examples are illustrative (but not restrictive):

EXAMPLE 1

Stabilizer Lactose 100 ml of methyltriethoxysilane are solubilized in a mixture of 80 g of water and 350 g of absolute ethanol. 1.1 kg of lactose monohydrate is then added to the solution (partially soluble), and the whole mixture is maintained under stirring at room temperature for 17 hours. The solvents are then progressively eliminated by distillation under reduced pressure (2000–2600 Pa) and moderate heat. Finally 1.12 Kg of a white pulverulent solid is obtained, which may be further transformed, by dissolution in water or in vivo, into a biologically active silanol with the same properties as the silanols from the prior art.

EXAMPLE 2

Stabilizer Hydrolized Collagen 100 g of hydrolyzed collagen are dissolved at 30° C. and under stirring in 900 g of distilled water. 1 liter of absolute ethanol is then added. 100 g of methyltriethoxysilane are then added drop by drop and under stirring to the mixture. The methyltriethoxysilane is not soluble in water but it hydrolyzes in soluble methylsilanetriol which combines with the polypeptides constituting the hydrolyzed collagen. Little by little, the mixture becomes limpid and homogenous. The solution is maintained under stirring at room temperature for 17 hours. Then the temperature is increased up to 50° C. before adding 300 g of hydrolyzed collagen. By the means of a diluted solution of chlorhydric acid, the medium is maintained, if necessary, at acidic pH. Ethanol and part of the water are then eliminated by distillation under reduced pressure (2000–2600 Pa) and moderate heat. A more or less gelified residue is obtained according to the nature of the hydrolyzed collagen and the quantity of acid added. Then an intense dehydration is carried out in order to finally obtain a colored, translucent solid which can be crushed into a slightly colored powder, perfectly soluble in water.

EXAMPLE 3

Stabilizer Hydrolyzed Collagen—Dispersant Cellulose 100 g of hydrolyzed collagen are dissolved at 30° C. and under stirring in 900 g of distilled water. 1 liter of absolute ethanol is then added. 50 g of methyltriethoxysilane are then added drop by drop and under stirring, to the mixture. The methyltriethoxysilane hydrolyzes in soluble methylsilanetriol which combines with the polypeptides constituting the hydrolyzed collagen. Rapidly the mixture becomes limpid and homogenous. The solution is maintained under stirring at room temperature for 17 hours. Then the temperature is increased up to 50° C. before adding 100 g of hydrolyzed collagen. By the means of a diluted solution of chlorhydric acid, the medium is acidified if necessary and then 200 g of micro crystalline cellulose are added. The mixture is maintained under stirring until perfect homogenization of the mixture (the cellulose is not soluble). Ethanol and part of the water are then eliminated by distillation under reduced pressure (2000–2600 Pa) and moderate heat. Then a intense dehydration is carried out in order to finally obtain a colored, translucent solid, which can be crushed into a slightly colored powder, perfectly soluble in water.

EXAMPLE 4

Stabilizer Hydrolyzed Wheat Proteins 200 g of an hydrolyzed wheat proteins are dissolved at room temperature in 500 g of distilled water. Then 500 ml of absolute ethanol are added. 25 g of methyltriethoxysilane are then added drop by drop and under stirring to the solution. The methyltriethoxysilane hydrolyses in methylsilanetriol at acidic pH which is accompanied by an homogenization of the mixture. The solution is maintained under stirring at room temperature for 17 hours. Ethanol and part of the water are then eliminated by distillation under reduced pressure (2000–2600 Pa) and moderate heat. Residual solvents are then eliminated under vacuum (13,332 Pa). 230 g of colored powder perfectly soluble in water are obtained.

EXAMPLE 5

Stabilizers: Salicylic Acid and Hydrolyzed Wheat Proteins 100 g of hydrolyzed wheat proteins is dissolved at room temperature in 1 liter of distilled water. The medium is acidified and 1 l of absolute ethanol are added progressively under stirring. 50 g of methyltriethoxysilane are then added drop by drop and under stirring to the solution. The solution becomes cloudy, then, rapidly becomes limpid and homogenous again. The solution is maintained under stirring at room temperature for 17 hours. Then, 300 g of hydrolyzed wheat proteins are added. After complete dissolution, the pH may be possibly adjusted with salicylic acid. Ethanol and part of the water are then eliminated by distillation under reduced pressure (2000–2600 Pa) and moderate heat. Residual solvents are then eliminated under vacuum (13,332 Pa). 460 g of colored powder perfectly soluble in water are obtained.

What is claimed is:

1. An organosilicon compound having the following formula (I):

$$R_4\text{—Si }(OR_1)\,(OR_2)\,(R_3) \tag{I}$$

wherein $R_1$ and $R_2$ each independently represent an atom of hydrogen or an alkyl group, $R_3$ represents an hydrogen atom, an hydroxyl group, an amine group, an alkyl group, an alkoxy or a carboxylate group, and at least one of the $OR_1$, $OR_2$ or $R_3$ groups represents an hydroxyl group, $R_4$ represents an alkyl group substituted by a phosphate or phosphonate group, and said compound is a solid.

2. The compound of claim 1, wherein $R_4$ represents a diethylphosphatoethyl group.

3. The compound of claim 1, wherein $OR_1$, $OR_2$ and $R_3$ each represent a hydroxyl group.

4. The compound of claim 2, wherein said compound comprises diethylphosphatoethylsilanetriol.

5. A composition comprising an organosilicon compound of the following general formula (I):

$$R_4\text{—Si }(OR_1)\,(OR_2)\,(R_3) \tag{I}$$

wherein $R_1$ and $R_2$ each independently represent an atom of hydrogen or an alkyl group, $R_3$ represents an hydrogen atom, an hydroxyl group, an amine group, an alkyl group, an alkoxy or a carboxylate group, and at least one of the $OR_1$, $OR_2$ or $R_3$ groups represents an hydroxyl group, $R_4$ represents an alkyl group substituted by a phosphate or phosphonate group, wherein said compound is a solid, and is associated with at least one stabilizer selected from the group consisting of aspartic acid, glutamic acid, lactic acid, salicylic acid, theophylline acetic acid, carboxylic pyrroldinone acid and a salt thereof, hydrolyzed elastin proteins, hydrolyzed spirulina, hydrolyzed collagen, hydrolyzed vegetal protein, elastin protein, spirulina protein, collagen protein, vegetal protein; lactose, glycosaminoglycanne and mucopolysaccharide.

6. The composition of claim 5, wherein said vegetal protein is oat protein or wheat protein.

7. The composition of claim 5, wherein said hydrolyzed vegetal protein is hydrolyzed oat protein or hydrolyzed wheat protein.

8. The composition of claim 5, wherein said mucopolysaccharide is selected from the group consisting of hyaluronic acid, pectin and alginic acid.

9. The composition of claim 8, wherein said mucopolysaccharide is hyaluronic acid.

10. The composition of claim 5, wherein said organosilicon compound is diethylphosphatoethylsilanetriol.

11. The composition of claim 5, further comprising a pharmaceutically acceptable excipient.

* * * * *